(12) United States Patent
Van Voorhis et al.

(10) Patent No.: US 6,618,128 B2
(45) Date of Patent: Sep. 9, 2003

(54) OPTICAL SPEED SENSING SYSTEM

(75) Inventors: J. Brent Van Voorhis, Kingston, TN (US); James C. Robinson, Knoxville, TN (US); Jason E. Hillard, Knoxville, TN (US)

(73) Assignee: CSI Technology, Inc., Wilmington, DE (US)

( * ) Notice: Subject to any disclaimer, the term of this patent is extended or adjusted under 35 U.S.C. 154(b) by 0 days.

(21) Appl. No.: 10/055,473

(22) Filed: Jan. 23, 2002

(65) Prior Publication Data

US 2003/0137648 A1 Jul. 24, 2003

(51) Int. Cl.$^7$ ................................................. G01P 3/36
(52) U.S. Cl. ........................................ 356/28.5; 356/28
(58) Field of Search .................................. 356/28, 28.5

(56) References Cited

U.S. PATENT DOCUMENTS

| | | | |
|---|---|---|---|
| 3,654,553 A | | 4/1972 | Mary et al. |
| 3,687,517 A | * | 8/1972 | Brun ........................... 356/28 |
| 3,689,157 A | | 9/1972 | Andermo |
| 3,804,517 A | | 4/1974 | Meyr et al. |
| 3,804,518 A | | 4/1974 | Meyr |
| 3,824,015 A | | 7/1974 | Petit et al. |
| 3,885,873 A | | 5/1975 | Andermo |
| 4,031,466 A | | 6/1977 | Krause et al. |
| 4,167,330 A | | 9/1979 | Haville |
| 4,181,432 A | | 1/1980 | Flower |
| 4,204,115 A | | 5/1980 | Boldridge, Jr. |
| 4,312,592 A | | 1/1982 | Sabater et al. |
| 4,329,047 A | | 5/1982 | Kikuchi et al. |
| 4,387,785 A | | 6/1983 | Fromm |
| 4,551,018 A | * | 11/1985 | Mannava et al. ........... 356/28.5 |
| 4,601,580 A | | 7/1986 | Halliwell |
| 4,638,155 A | | 1/1987 | Dorr |
| 4,774,463 A | | 9/1988 | Mizobuchi et al. |
| 4,866,268 A | | 9/1989 | Tang et al. |
| 4,880,966 A | | 11/1989 | Goodrich et al. |
| 4,968,145 A | | 11/1990 | Takiguchi |
| 5,059,901 A | | 10/1991 | Van Voorhis |
| 5,214,278 A | | 5/1993 | Banda |
| 5,365,787 A | | 11/1994 | Hernandez et al. |
| 5,424,824 A | * | 6/1995 | Daiber et al. ............... 356/28.5 |
| 5,445,028 A | | 8/1995 | Bianchi et al. |
| 5,501,226 A | * | 3/1996 | Petersen et al. ............ 356/28.5 |
| 5,526,109 A | * | 6/1996 | Johnson ..................... 356/28.5 |
| 5,541,732 A | | 7/1996 | Forin |
| 5,612,544 A | | 3/1997 | Busch |
| 5,636,014 A | | 6/1997 | Hanson |
| 5,646,340 A | | 7/1997 | Gee et al. |
| 5,701,172 A | * | 12/1997 | Azzazy ........................ 356/28 |
| 5,872,628 A | * | 2/1999 | Erskine ...................... 356/28.5 |
| 6,233,045 B1 | * | 5/2001 | Suni et al. .................. 356/28.5 |

* cited by examiner

Primary Examiner—Stephen C. Buczinski
(74) Attorney, Agent, or Firm—Luedeka, Neely & Graham, P.C.

(57) ABSTRACT

An apparatus for determining the rotational speed of an object returning diffuse reflections where no reflective singularity exists on the object or no clearly distinct light pulse is produced. A light source illuminates a target area on the object. An optical system receives the reflected light, selectively filters by wavelength, and focuses the light on a detector for signal processing. The reflected light signals may be a series of complex patterns that repeat once per revolution. A Fourier Transform with additional processing enhancements is performed on the signals and used as a basis to calculate the speed of the object The signal processing may be automated, resulting in a speed (RPM) solution being displayed for the operator of the device.

25 Claims, 15 Drawing Sheets

OPTICAL SPEED SENSING SYSTEM

FIELD OF THE INVENTION

This invention relates generally to speed sensing devices. More particularly, this invention relates to a speed sensing device for determinig the speed of a rotating object, for example, a shaft, utilizing an optical system operable to determine the rotational speed from a diffuse reflective spectra where no reflective singularity exists and not requiring the use of a reflective element on the rotating object.

BACKGROUND

Customarily, when using an optical-type tachometer, it is necessary to apply a piece of retro-reflective tape or paint to a rotating machine element to provide a reflective target. When illuminated by a beam of light, the reflective target provides a distinct reflective signal which may be detected and processed to determine the rotational speed of the machine element. Alternatively, certain tachometer techniques utilize an area of a shaft where a single discontinuity exists, such as a flat or keyway. Reflections can be specular (mirror-like), diffuse (scattered), or a combination of the two.

A retro-reflector is a special case, wherein the reflected beam of light returns along a path incident to the illuminating light beam. Normally, for retro-reflective targets, the reflected beam exhibits only a small amount of divergence. Correspondingly, retro-reflective techniques provide for the maximum light return from the target. However, it is not always convenient or possible to affix a retro-reflective target to a machine element, since the machine may be operating or difficult to access. Moreover, the machine elements may be coated with oil or other fluids making adhesion of a reflector difficult, for example, a felt conveyor belt as used in a paper mill. Often it is necessary to use the trademark or other symbols which are dyed into a fabric as a target for an optical tachometer. Typically, these target types provide a very diffuse reflection, severely limiting the operational distance of optical-type speed sensors. Additionally, debris and moisture accumulating on the optics at close operating distances makes a longer operating distance desirable.

Optical tachometers utilize a single reflective discontinuity per revolution of a machine element to develop a single electrical pulse. The accuracy of the optical tachometer is based on the electrical pulse occurring at the same physical point on the machine element each revolution. This fundamental principle is necessary for the accurate measurement of the time between pulses for determining the rotational speed of the machine element. Moreover, it is also important for determining the phase relationship of frequencies within a vibration signal when monitoring the vibration spectrum of a machine. As an example, it is often desirable to know the phase and amplitude of the vibration component at one times running speed (1×revolutions per minute.). This phase measurement, locked to some physical orientation of a shaft, is fundamental to balancing machines and determining operating deflection shapes.

What is needed, therefore, is a speed sensor that does not require the application of a reflective target and is operable to determine the speed of a rotating object, such as a rotating shaft.

SUMMARY

The optical speed sensing system according to the invention advantageously provides speed measurements where it is difficult or impossible to obtain a distinct reflected light pulse from a rotating object. This is particularly advantageous in portable route based applications. Additionally, the system is operable to provide a convenient determination of the running speeds of a large number of operating machines having no reference marks or difficult to access marks. Surface irregularities of an object provide an intensity-modulated reflection when the rotating object is illuminated by the coherent light source. The same light intensity patterns are repeated once per revolution of the rotating object.

An apparatus and method are provided for determining the rotational speed of a rotating object, without requiring the location of a reflective target on the object. The apparatus includes a light source for transmitting a collimated light beam having a selected wavelength directly at the rotating object. Light signals are reflected from the rotating object, due to the transmission of light at the object. An optical system focuses the reflected light signals onto a single detection region of a detector. The detector is operable to detect the focused light signals and generate electrical signals based on the signals reflected and focused by the optical system. An analyzer analyzes the electrical signals representative of the reflected light signals. The analyzer includes a Fourier Transform function for transforming the electrical signals providing spectra representative of the electrical signals. The analyzer operates to determine and output the rotational speed of the rotating object based thereon. A power source is included for providing power to the apparatus.

A manual and an automated method are available to users of the apparatus in determining the speed of a rotating object.

BRIEF DESCRIPTION OF THE DRAWINGS

Further advantages of the invention will become apparent by reference to the detailed description of preferred embodiments when considered in conjunction with the figures, which are not to scale, wherein like reference numbers, indicate like elements through the several views, and wherein.

DETAILED DESCRIPTION

Figure 1:
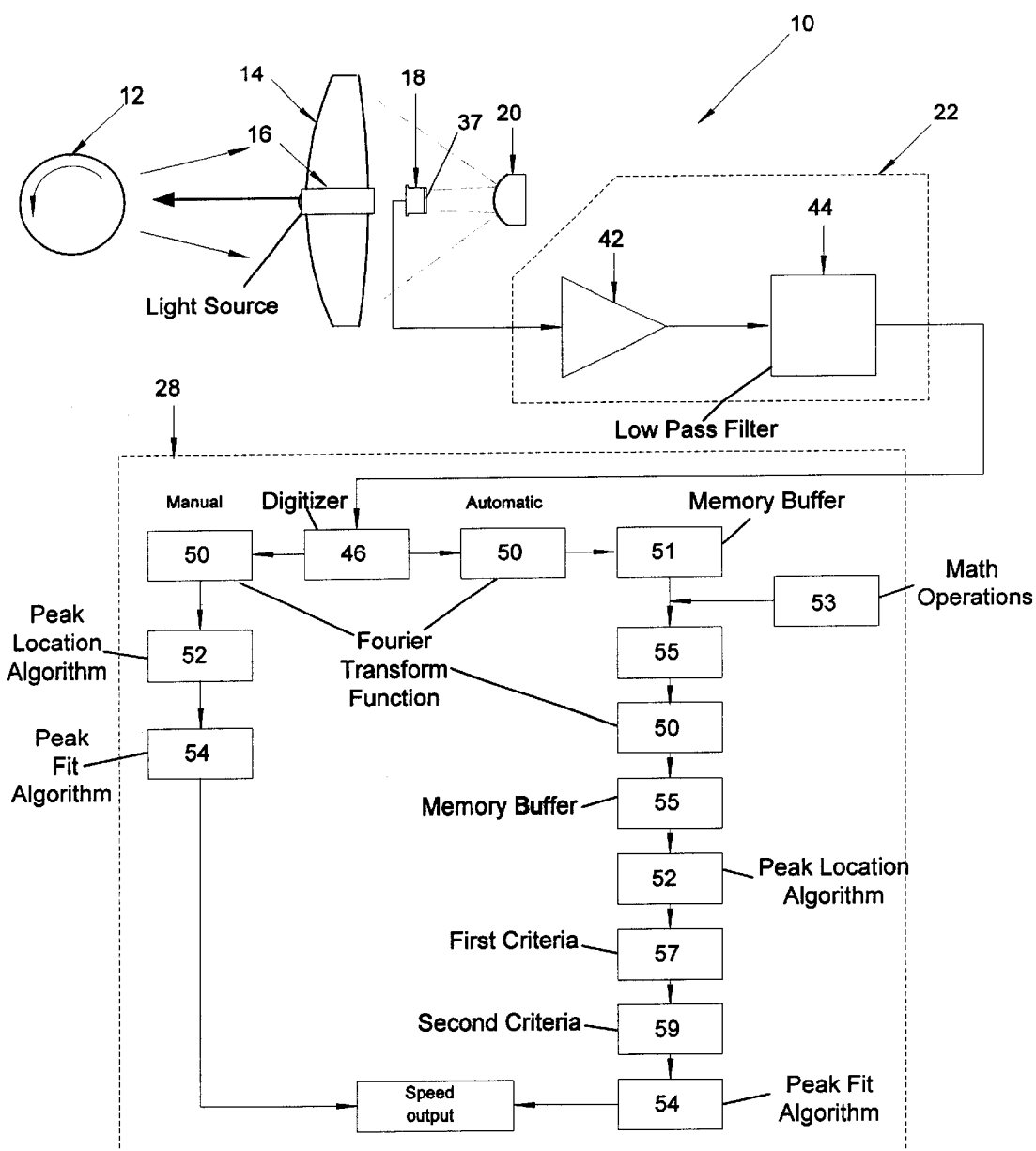
FIG. 1 is a depiction of an optical speed sensing system.
Figure 2:
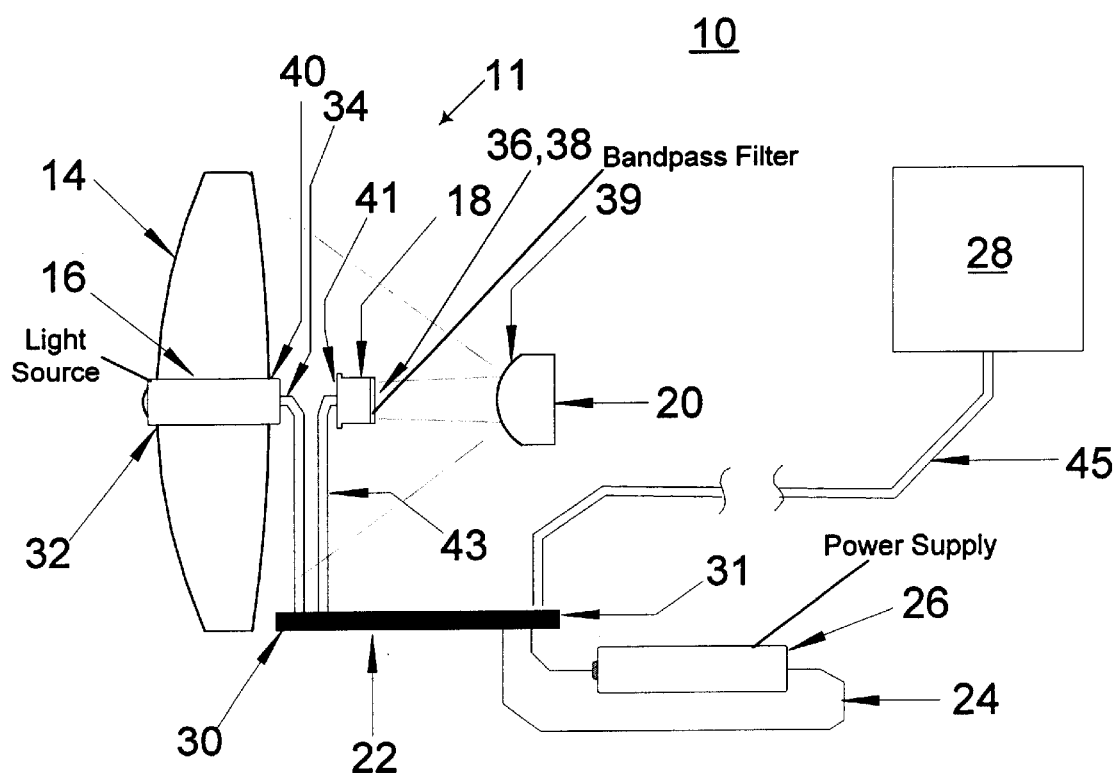
FIG. 2 is a side-view of the optical speed sensing system of FIG. 1.

Referring now to the Figures in which like reference numerals indicate like or corresponding features, there is shown in FIGS. 1 and 2 an optical speed sensing system 10. FIGS. 1 and 2 also depict various signal processing components for determining the rotational speed of a rotating object 12, such as a rotating shaft, for example. It will be appreciated that system 10 is operable to determine the rotational speed of various rotating objects, and is not intended to be limited by any examples discussed herein. The optical speed sensing system 10 advantageously provides speed determinations without having to apply a reflective target to the object 12. The optical speed sensing system 10 can also provide speed determinations without the existence of a reflective singularity or singular reflective discontinuity.

The optical speed sensing system 10 provides enhanced sensing of the rotational or translational speed of an object 12, such as a machine element, etc. exhibiting substantially diffuse reflections from either natural or man-made discontinuities on a relatively uniform surface of the object 12. However, it should be understood that the system 10 is not limited to operation on the type of reflections from any specific object. For example, the optical speed sensing system 10 can determine the rotational speed of an object 12 exhibiting one or more substantially specular reflections per revolution, as well.

In one embodiment, the optical speed sensing system 10 includes an optical speed sensor 11 and an analyzer 28 (FIG. 2). Preferably, the optical speed sensor 11 incorporates a collecting lens 14, light source 16, detector 18, focusing member 20, circuit board 22, electrical connectors 24, and power supply 26. The light source 16 is preferably a visible light laser diode "micro" module operable to transmit a collimated laser beam at a wavelength of about 650 nanometers. However, it is appreciated that other light sources may be used in the optical speed sensing system 10.

The light source 16 is preferably mounted integrally with the collecting lens 14 and is located at a first end 30 of the circuit board 22. By integrating the light source 16 with the collecting lens 14, it becomes possible to present a compact, and freely operable optical speed sensing system 10, as described further below. The compactness of the optical speed sensing system 10 enables a user to access more limited areas when determining the rotational speed of an object 12. Furthermore, the optical speed sensing system 10 is advantageously configured in coaxial alignment by centrally locating the light source 16 proximate the central bore 32 of the collecting lens 14. Thus, excessive and time-consuming alignment of the components of the optical speed sensing system 10 is unnecessary.

As described above, the light source 16 is operable to transmit a collimated light beam, preferably a laser beam, towards the object 12. Preferably, the light source 16 transmits a collimated light beam directly at the object 12, imaging only one region on the rotating object 12. Since the laser diode module incorporates an integral focusing lens, it is most preferred that no additional optical focusing or splitting components accompany the laser beam transmission. Thus, a maximal amount of beam energy is directed at the object 12 because there are no obstructions in the laser beam path, i.e. the collimated light beam is transmitted directly at the object 12. Since a maximal amount of beam energy is transmitted towards the object 12, the amount of light reflected from the object 12 is correspondingly maximized.

The collecting lens 14 or objective lens, preferably has a diameter of between about 30 millimeters to about 50 millimeters. The collecting lens 14 is preferably constructed of a plastic, such as acrylic, and has an aspherical design. For enhanced light transmission, an antireflection coating may be applied to the collecting lens 14. As described above, the collecting lens 14 preferably contains a central hole or bore 32 piercing the collecting lens 14. The central bore 32 facilitates mounting of the light source 16, allowing power leads 34 to be attached to the light source 16 and electrically connected to the circuit board 22.

As described below, the circuit board 22 is electrically connected to the analyzer 28. In a preferred embodiment of the invention, the powered up analyzer 28 provides power to the circuit board 22 and the electrical components of the optical speed sensor 11. Alternatively, a DC battery source can be used as the power source 26, providing power to the light source 16 and electrical components of the optical speed sensing system 10.

While the mounted light source 16 is a central obstruction in the optical path of the collecting lens 14, the small area blocked by the light source 16 is insignificant in view of the total light collecting area of the collecting lens 14. The micro-laser module described above, commercially available from NVG Incorporated of Hazlehurst, Georgia, has a diameter of about 0.25 inches or 6.35 millimeters, representing an area of about 31.7 millimeters$^2$. The unobstructed area of a 30 millimeter collecting lens 14 is about 707 millimeters$^2$. Thus, the micro-laser module obstructs only about 4.5% of the light collecting area of the collecting lens 14. For a collecting lens 14 having a 50 millimeter diameter, the light source 16 obstructs on area.

As the light source 16 transmits a single collimated light beam directly at the rotating object 12, the collecting lens 14 collects the light reflected from the object 12. The reflected light collected by the collecting lens 14 is directed by the collecting lens 14 at the focusing member 20, as described in more detail below. As used herein, and as will be appreciated, the term, "focusing member", is not meant to limit the system 10 to any specific structure, configuration, or quantity.

In a most preferred embodiment of the invention, as best shown in FIGS. 1 and 2, the focusing member 20 is a convex spherical or hyperbolic mirror. A convex spherical mirror used as the focusing member 20 is an economical choice, the mirror having sufficient optical performance to direct the light to a desired location. However, other focusing configurations are available, as will be described below. The focusing member 20 re-directs the collected light from the collecting lens 14 onto the active sensing surface of the detector 18.

The detector 18 is preferably a photodiode 36 having an integral optical bandpass filter 38. The integrated detector 18 is commercially available from Intor, Inc. of Socorro, N. Mex. The integrated detector 18 is operable to detect reflected signals within a frequency range determined by the bandwidth of an optical bandpass filter 38. Preferably, the optical bandpass filter 38 has a bandwidth of about 20 nanometers. Thus, only a portion of the light reflected from the object 12, which is in a narrow spectral range preferably centered at a wavelength of about 650 nanometers, passes through the optical bandpass filter 38.

The filtered light impinges upon the active area of a photodiode 36, wherein the photodiode 36 is responsive to light having a wavelength of about 650 nanometers. Most preferably, the active area of the photodiode 36 is a single continuous sensing area or detection region 37 (FIG. 1), which receives the light signals directed by the focusing member 20 and passed by the optical bandpass filter 38.

The detector 18 preferably has one output 41, outputting analog time domain signals representative of the reflected light intensity patterns reflected by the rotating object 12. More particularly, the photodiode 36 incorporated into the detector 18 is operable to convert the light intensity patterns reflected by the focusing member 20 to analog electrical time domain signals. As described below, the signal processing components process the signals corresponding to the light signals received by the single detection region 37 of the detector 18 to determine the rotational speed of the object 12.

Preferably, as shown in FIGS. 1 and 2, the detector 18 is mounted coaxially proximate the rear end 40 of the light source 16. In this embodiment, the detector 18 is mounted so that the active area of the photodiode 36 and integral bandpass filter 38 face toward the rear 31 of the optical speed sensor system 10, the active area of the photodiode 36 facing the reflecting surface 39 of the focusing member 20. The preferable focusing member 20, a convex mirror, is mounted so that substantially all of the radiant flux exiting the collecting lens 14 impinges upon the mirror. The focusing member 20 is adjusted relative to the collecting lens 14 so that the reflected beam is preferably collimated or made slightly converging so that the entire reflected beam area impinges upon the active area of the photodiode 36.

The photodiode 36 produces analog electrical signals representative of the reflected light intensity patterns from the focusing member 20. The analog electrical signals produced by the photodiode 36 are conditioned by various components mounted on the circuit board 22. Preferably, the circuit board 22 includes an amplifier 42 and a filter, preferably a low-pass filter 44. The analog electrical signals produced by the photodiode 36 and output from the output 41 of the detector 18, are transmitted along the electrical connections 43, amplified by the amplifier 42 and filtered through the low-pass filter 44 before being passed to the machinery analyzer 28.

The machinery analyzer 28 includes various digital signal-processing components 46 for digitizing the analog signals, and additional firmware (FIG. 1). One such analyzer 28 is the CSI Model 2120, manufactured by Emerson Process Management/CSI of Knoxville, Tennessee. An alternative analyzer 28 having additional processing options is the CSI 2120A Machinery Analyzer, also manufactured by Emerson Process Management/CSI of Knoxville, Tenn. The analog electrical signals provided by the photodiode 36 are preferably transmitted by direct cable link 45 to the analyzer 28, although other transmission means are available, such as radio frequency or infra-red transmission techniques.

As described above, the signals presented to the analyzer 28 are analog electrical time domain signals, having complex signal patterns. These complex signal patterns repeat once per revolution of the object 12. The user of the speed sensing system 10 may elect, through inputs to the analyzer 28, to manually proceed with the analysis of the time domain signals to determine the rotational speed of the rotating object 12. Through various inputs, the user configures the analyzer 28 to perform a Fourier Transform upon the time domain signals, utilizing a Fourier Transform function 50 included in the analyzer 28. For example, for the manual mode of speed determination, the user may elect to input a value for Fmax. Fmax corresponds to a maximum display frequency and maximum lines of resolution. That is, selection of Fmax provides a finite number of data points (or some number of Hertz per frequency bin) for the analysis of the signals by the analyzer 28. It is appreciated that the Fourier Transform function 50 may include other processing capabilities, including discrete Fourier and fast Fourier processing.

After the digital signal processing components 46 process the analog signals to a digital format, the Fourier Transform function 50 converts the digital time domain signals to the frequency domain, creating power spectral density data or frequency spectra, and more particularly, a speed spectrum. The speed spectrum corresponds to the reflected signals by the rotating object 12.

Included in the base firmware of analyzer 28 are peak location algorithm 52 and peak fit algorithm 54 (FIG. 1). Due to a finite number of frequency bins, the algorithms enhance the frequency measurement accuracy of analyzer 28 by interpolation between the frequency bins. When incorporated as part of the optical speed sensing system 10, the analyzer 28 displays a speed spectrum. The peak location algorithm 52 and peak fit algorithm 54 operate on the frequency domain signals. The peak location algorithm 52 can locate the fudamental peak of the lowest order major harmonic family, or the harmonic family of another user selected peak within the frequency spectra provided by the Fourier Transform function 50. The analyzer 28 also includes a peak fit algorithm 54 which "fits" a curve to the frequency spectra, including the higher amplitude peaks in a harmonic family. The peak fit algorithm 54 increases the precision of the frequency measurement by interpolating between the finite number of frequency bins, enhancing the location of a peak and the accuracy of the speed measurement provided by the speed sensing system 10.

In the manual mode, the user of analyzer 28 may place a cursor on a frequency peak believed to be representative of the running speed of the object 12. The peak location algorithm 52 and peak fit algorithm 54 operate on the speed spectrum to enhance the selection of a peak by the user. If the harmonic cursors are enabled by the user, the analyzer 28 will determine the major harmonic family of the frequency spectra associated with the user selected frequency peak. The analyzer 28 determines the frequency of the user selected peak, which is frequently the lowest order peak of the major harmonic family in the speed spectrum, indicating the rotational speed of the object 12. The analyzer uses the user selected peak to calculate the revolutions per minute (RPM). Specifically: (frequency in Hertz)×60=revolutions per minute of the object 12. The analyzer's display displays the speed to the user as calculated by the analyzer 28.

Figure 3:
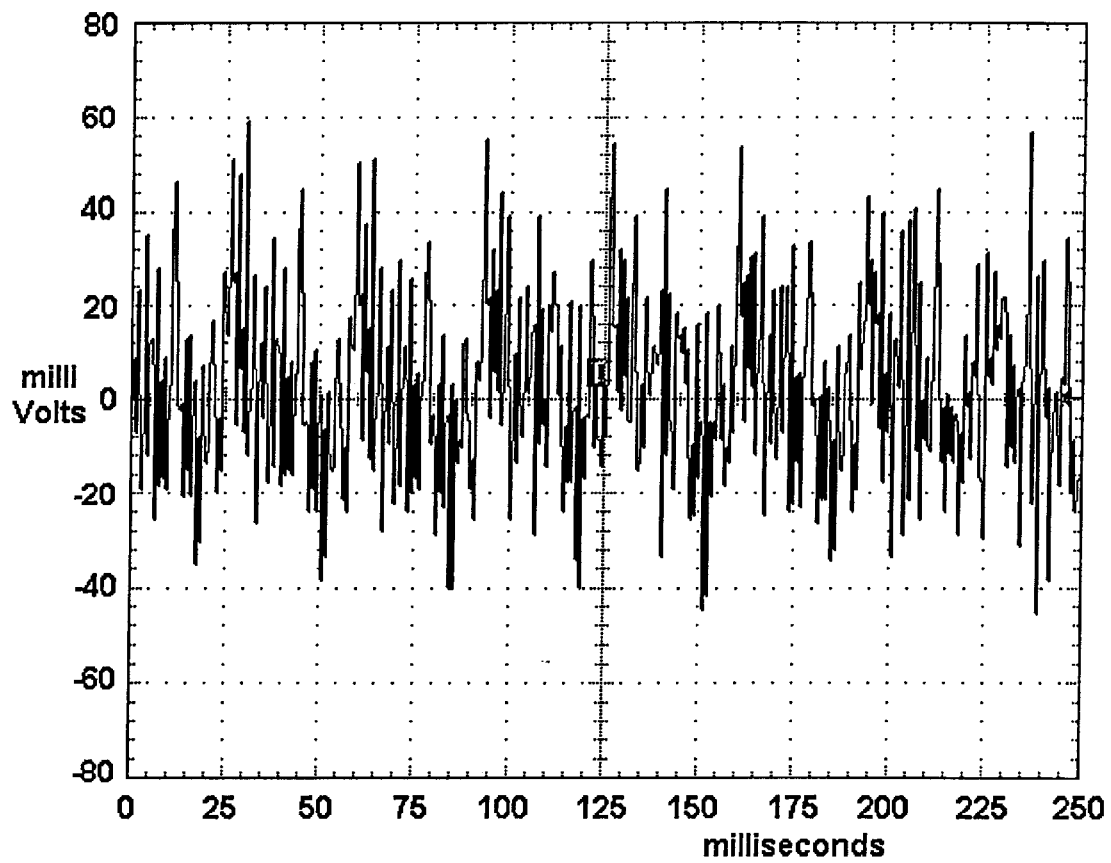
FIG. 3 is a graph illustrating an analog signal output from a component of the optical speed sensing system.
Figure 4:
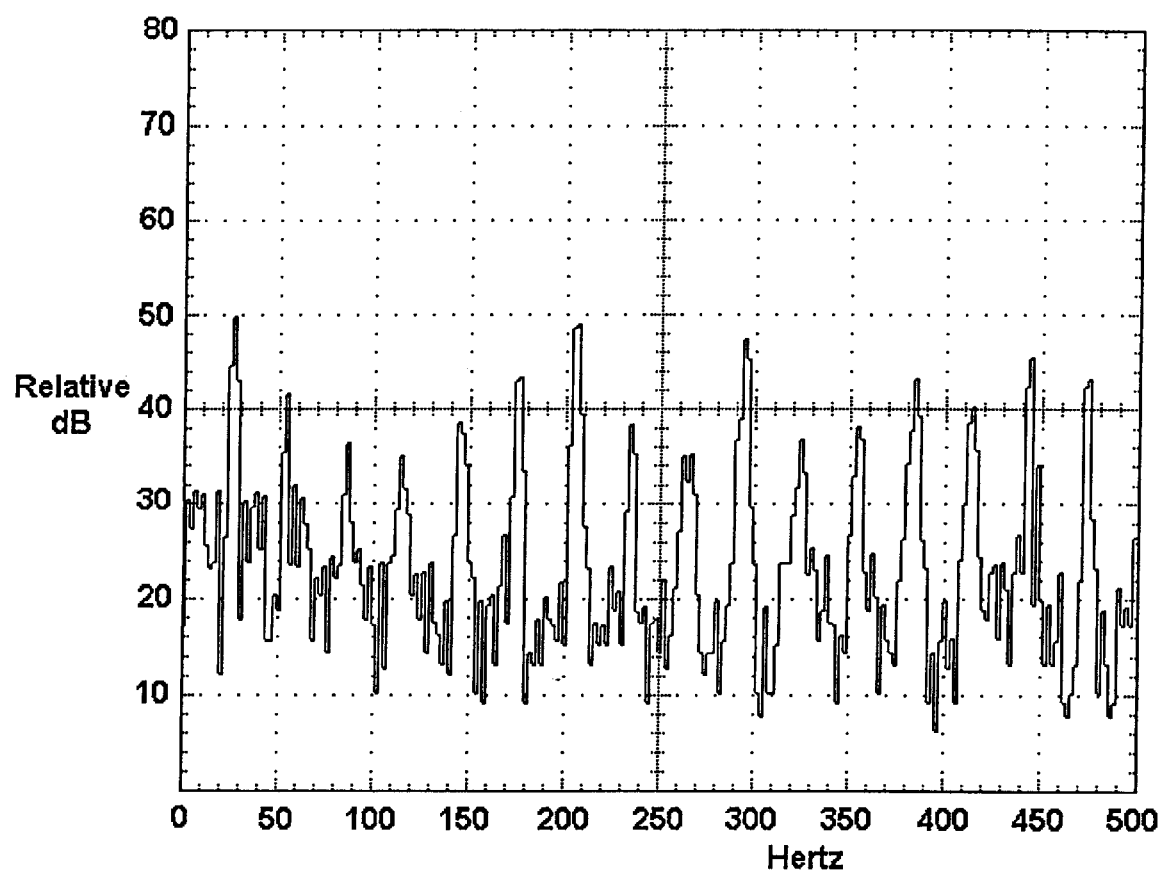
FIG. 4 is a graph of frequency spectra after an application of a Fourier Transform function to the analog signal of FIG. 3.

For example, FIG. 3 depicts the analog time domain signals output from the photodiode 36 for a rotating section of white felt belting. As shown in FIG. 3, the time domain signals corresponding to the reflection from white felt belting exhibit no distinctive discontinuities in reflectivity, or no single pulse per revolution that can be easily recognized as corresponding to the rotational speed of object 12. With additional reference to FIG. 4, after processing the digitized signals with the Fourier Transform function 50 of the analyzer 28, the lowest order frequency in the major harmonic family is seen to be about 27 Hertz, indicative of a motor running speed of about 1650 revolutions per minute (27 Hertz×60).

In a most preferred embodiment, an automated method of speed measurement is used to determine the rotational speed of the object 12 (FIG. 1). For the automated method, user inputs to the analyzer 28 are minimal. It is preferred to use an analyzer 28, such as the CSI 2120A Machinery Analyzer, as described above. As described further below, the system 10, upon receiving the analog electrical time domain signals from the optical speed sensor 11, automatically provides the rotational speed of the object 12 to a user.

As described above, the reflected signals from the rotating object 12 are converted to analog electrical signals by the detector 18, and output from the optical speed sensor 11 to the analyzer 28. The analyzer 28 converts the analog signals to the digital domain (digitized signals) through its digital signal processing components 46.

After digitizing the analog electrical signals output from the detector 18, the analyzer 28 uses the Fourier Transform function 50 to generate a speed spectrum from the digitized signals. During this time, the analyzer 28 also maintains the digitized data or time waveform data in memory contained in the analyzer 28. It is preferred to carry out successive, and most preferably two Fourier Transform operations using the Fourier Transform function 50 on the digitized signals, thereby providing autocorrelation data for subsequent analysis by the analyzer 28 (FIG. 1). That is, for the automated method, it is most preferred to first apply the Fourier Transform function 50 on the digitized signals to generate a speed spectrum. Then, applying the Fourier Transform function 50 on the speed spectrum to provide the autocorrelation data. It is appreciated that the term "autocorrelation data" is not intended to limit the invention to any specific autocorrelation theories, etc. As described below, the analyzer 28 uses the autocorrelation data to provide a rotational speed determination to the user.

The autocorrelation data is used in conjunction with a set of criteria, to automatically determine the rotational speed with a high degree of confidence, as described in detail below. The goal of autocorrelation is to find the similarities or "correlation" between a signal and a delayed version of the signal. Reflected light signal patterns by the rotating object 12 that are periodic in nature (repeat once per revolution) appear highest in amplitude in the autocorrelation data or on a displayed autocorrelogram, such as that shown in FIG. 7 for a simulated signal. The periodic signal or signals are usually harmonic in nature and are revealed in the autocorrelation data as peaks in multiples of the fundamental frequency.

Additionally, signals that have little or no periodicity will not appear in the autocorrelation data. Random noise, such as random light reflections from rotating object 12 or other stray light signals that might be included in the input signal sample, are generally not periodic in nature. As such, these nonperiodic signals will not appear in the autocorrelation data. This has the effect of "unmasking" the desired periodic signals that are often not visible or recognizable in a simple time domain waveform. This enables the speed of rotating object 12 to be determined even where the object 12 has no apparent surface irregularities.

FIGS. 5–9 depict time waveforms and spectra generated by simulating a return reflection from a rotating object 12. An approximate 29.1 Hz. pulse generated by a finction generator was input to the analyzer 28 instead of inputting a signal from the detector 18. This was done in order to simplify the following discussion, generating less complex spectra than generally produced by rotating machinery.

Figure 5:
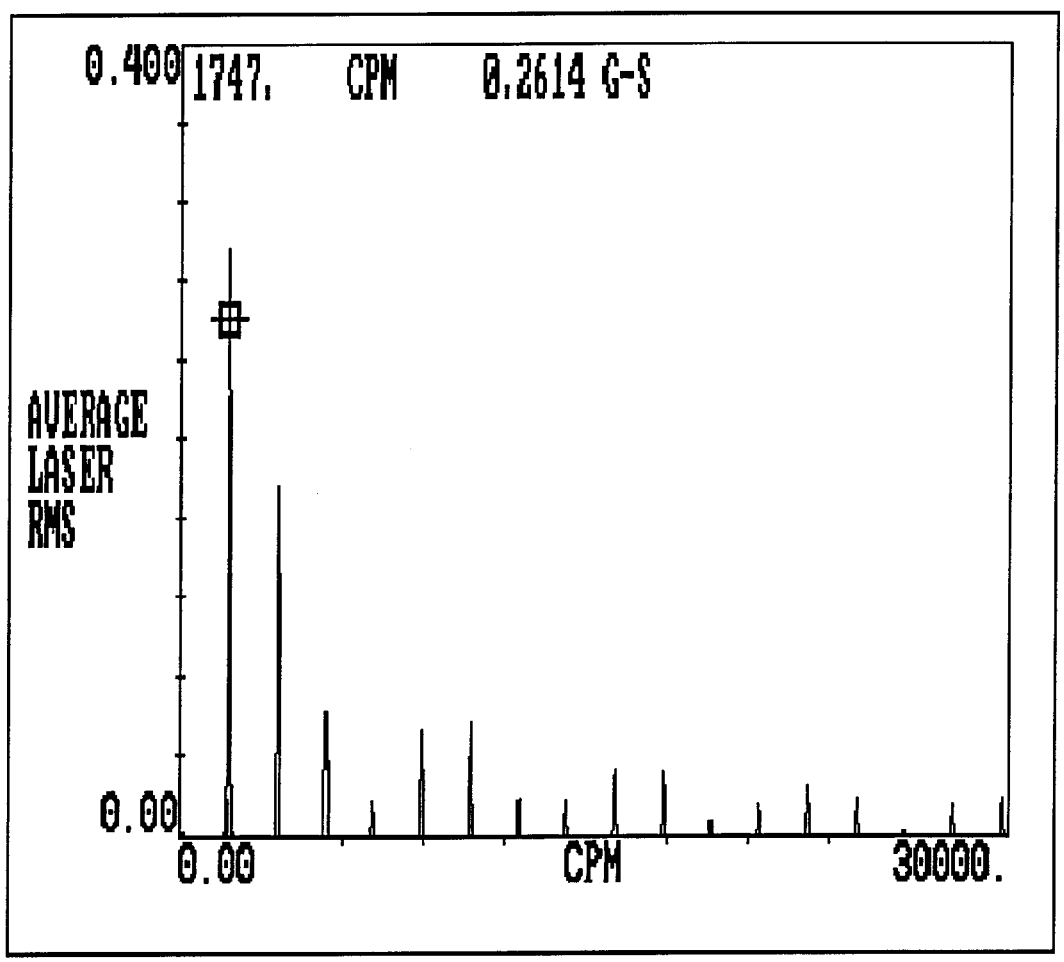
FIG. 5 depicts frequency spectra after a first application of a Fourier Transform function upon a simulated input signal.

FIG. 5 depicts frequency spectra corresponding to the simulated signal generated by the Fourier Transform function 50. The frequency spectrum data or spectra are used by the system 10 in determining the rotational speed. After generating the frequency spectrum data, the analyzer 28 packs and stores the data into memory buffers. The data, however, is not yet displayed to the user on the analyzer display. The analyzer 28 preferably includes two 16K memory buffers, herein termed first memory buffer 51 and second memory buffer 55 for storing the data. The first memory buffer 51 contains the frequency spectrum data output by the first application of the Fourier Transform function 50 to the digitized data. This data is preserved because the frequency spectrum including the speed determination is subsequently displayed to the user, as described further below.

Figure 6:
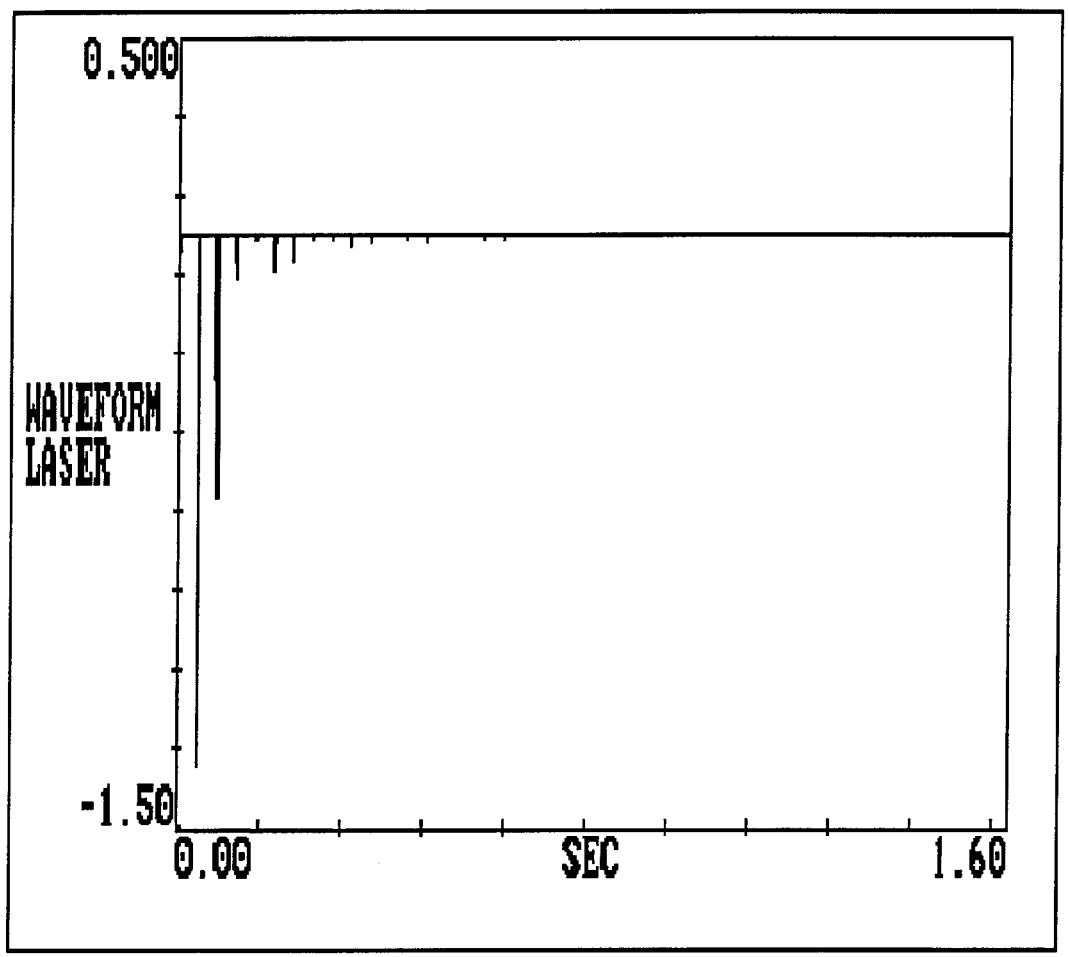
FIG. 6 is a time waveform plot (shown inverted) corresponding to FIG. 5.

At this point, the second memory buffer 55 is preferably filled in with zeros or reset. Before transferring the frequency spectrum from the first memory buffer 51 to the second memory buffer 55, the data is conditioned by math operations 53. Each data point in the first memory buffer 51 is preferably squared, and then converted to an integer in the range of about zero to about 32767. The analyzer 28 uses this range of data to generate a time waveform plot (FIG. 6). At this point, memory buffer two 55 contains the data points from memory buffer one 51 that have been converted to integers. The data in memory buffer one 51 preferably does not change.

To remove any DC offset, the analyzer 28 preferably sets the first two data points in the second memory buffer 55 to zero. Zeros are used to fill in any excess data points in the second memory buffer 55 (FIG. 6). Next, the analyzer 28 applies a second Fourier Transform to the data in the second memory buffer 55 again using the Fourier Transform function 50 on the data, providing autocorrelation data. Preferably, the analyzer 28 applies a uniform window during the application of the Fourier Transform fuinction 50 for the second time to obtain the autocorrelation data. It is also preferred to use a hanning window during the first application of the Fourier Transform function 50.

Figure 7:
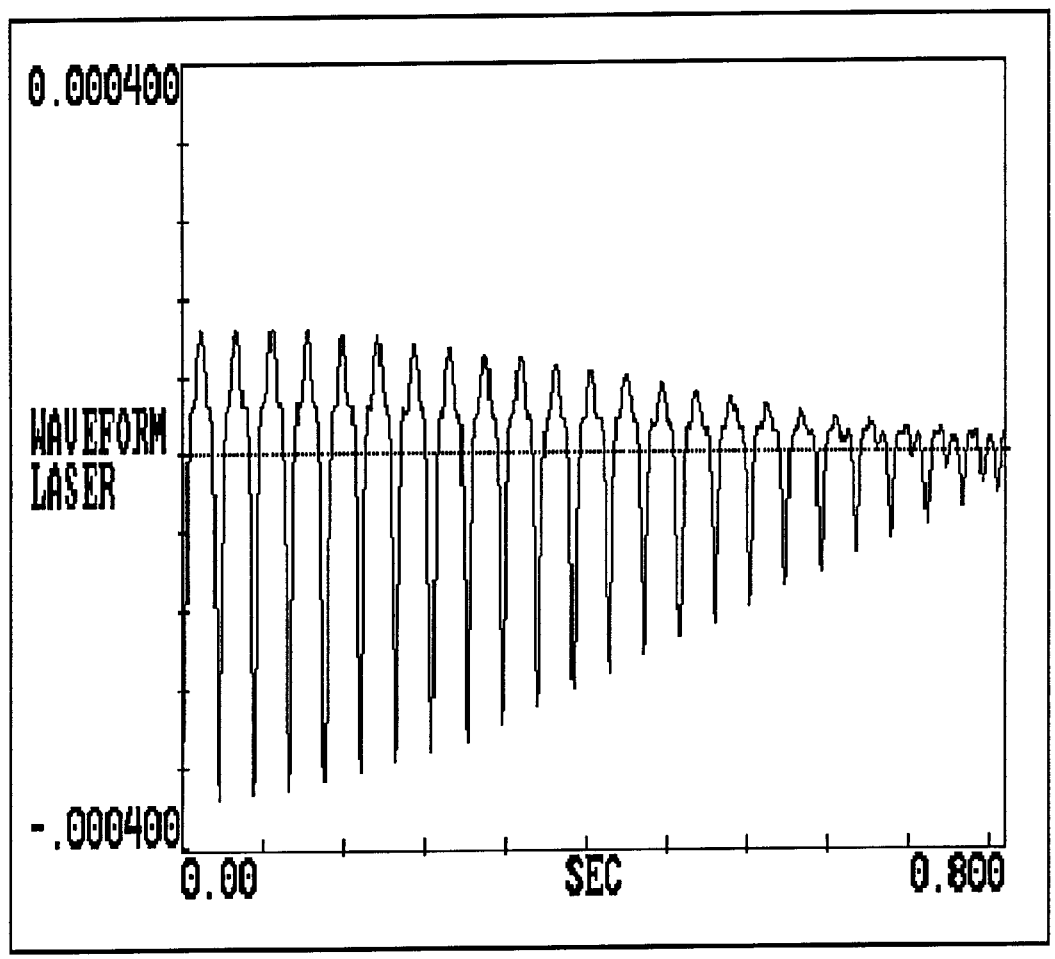
FIG. 7 is a time plot (autocorrelogram) (shown inverted) after a second application of a Fourier Transform function.
Figure 8:
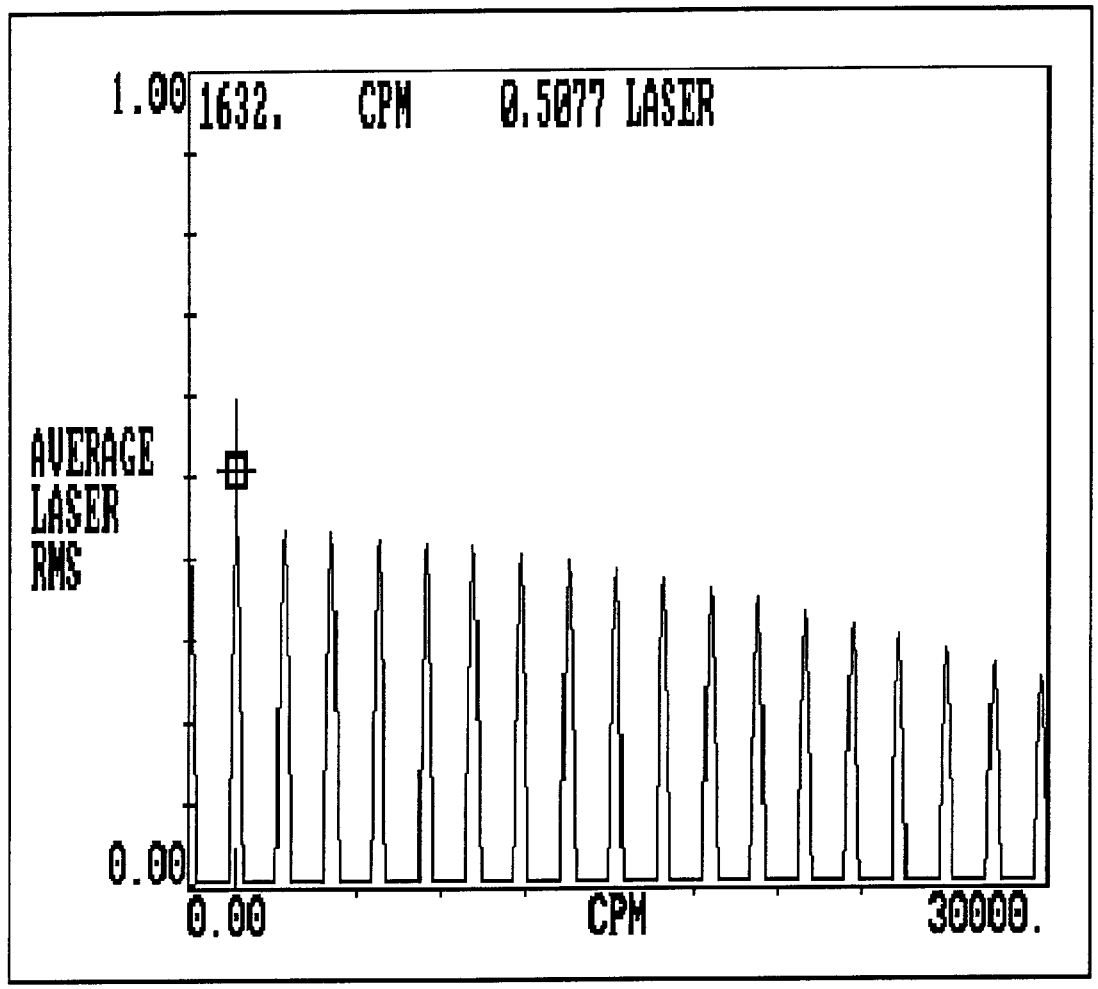
FIG. 8 is an autocorrelogram frequency plot output from the system after a second application of a Fourier Transform function.

After applying the Fourier Transform function 50 for the second time, obtaining real and imaginary data, the analyzer 28 reads and stores the real portion of the data into the second memory buffer 55. Preferably, negative values are set to zero and the positive values are squared before being stored. While the analyzer 28 does not actually display the data, FIG. 7 is shown for reference, and depicts Fourier Transform real data on a time plot ("autocorrelogram"). Although the data is actually time data, the analyzer 28 does not perform a peak search on a time plot, so the data is transferred directly to a spectral plot. FIG. 8 depicts the analyzer's output of the Fourier Transform real data on a spectral plot, i.e. autocorrelation data transferred to a frequency plot, for the simulated signal. The analyzer 28 then utilizes the peak location algorithm 52 on the data stored in the second memory buffer 55 to determine the twenty largest peaks, for example. Normally, the first few peaks are of highest amplitude, and the peak location algorithm 52 preferably determines the rotational speed of the object 12 when a first peak satisfies the following criteria 57:

A. The peak is not located in one of a first set of frequency bins (preferably the first ten), B. The peak amplitude is greater than about 0.30 multiplied by the largest amplitude on the plot (a select bin), and C. There is a peak located at about two times the peak frequency (+or−Delta-F) that also satisfies the criteria in A and B.

After a peak is chosen meeting the required criteria, another step is performed to check for another peak that the search routine might have missed. In the case of a repeating pattern, such as a pattern produced by fan blades and gear teeth, the reflected signal may have a plurality of reflective singularities of substantial amplitude. This will add many more peaks to the autocorrelation plot. In some cases, there can be more than 120 peaks. These peaks can vary in amplitude, and the first few peaks may not always be the largest.

Continuing the example, the analyzer 28 only picks out the 20 largest peaks. However, the first few peaks may not be included in the list, resulting in the peak location algorithm 52 not selecting the correct peak. To solve this problem, when the analyzer 28 is performing the peak search to store the 20 largest peaks, the analyzer 28 also stores the first 10 peaks for example, regardless of amplitude. The peak location algorithm 52 proceeds as previously described and chooses a peak from the list of 20. At this point, the list of the first 10 peaks is searched to see if there is a peak that meets the following criteria 59:

A. The peak amplitude is greater than about 0.90 multiplied by the amplitude of the originally chosen peak.

B. There is a peak located at about two times the new peak frequency (+or−Delta-F) that also satisfies the criteria in A.

If a peak matches the above criteria, then the peak is chosen.

Table 1 lists the first nine peaks obtained using the peak location algorithm 52 for the simulated signal.

TABLE 1

| Frequency (Cycles per minute (CPM)) | Magnitude (G's) |
|---|---|
| 1632 | 0.5077 |
| 3282 | 0.5039 |
| 4933 | 0.4990 |
| 6582 | 0.4941 |
| 8233 | 0.4871 |
| 9883 | 0.4800 |
| 11533 | 0.4708 |
| 13183 | 0.4624 |
| 14833 | 0.4496 |

By meeting the above criteria, the peak chosen from the autocorrelation data will be the first peak from a group of harmonic peaks that occur in multiples of the fundamental frequency. Each harmonic peak is separated by the amount of time for one revolution of the rotating object 12. The chosen peak is the first peak, offset from zero time by the amount of time for one revolution of the rotating object 12, therefore representing the turning speed. However, the data, which is actually time data, is still on a spectral plot. The chosen peak value must be converted to an offset on the time scale.

According to this most preferred embodiment, the analyzer 28 converts the chosen peak according to the selection criteria back to time format. More particularly, the analyzer 28 divides the chosen peak frequency by Delta-F, and then multiplies this result by Delta-T. The result is a "best approximation" of the rotational speed of the object 12. This "best approximation" is then used by the analyzer 28 as the cursor location on the original frequency spectrum stored in the first memory buffer 51, which is displayed on the analyzer display to the user, thereby providing a best approximation of the speed to the user.

As used herein, Delta-F =(Fmax/number of lines of resolution). (Delta-T 1/(Fmax multiplied by 2.56)). However, it is appreciated that the special and criteria may be changed according to each speed determination. For the automated method, the analyzer 28, according to the speed range selected by the user, automatically determines Fmax and the number of lines of resolution. The resolution obtained is defined as the spacing between each data point.

Figure 9:
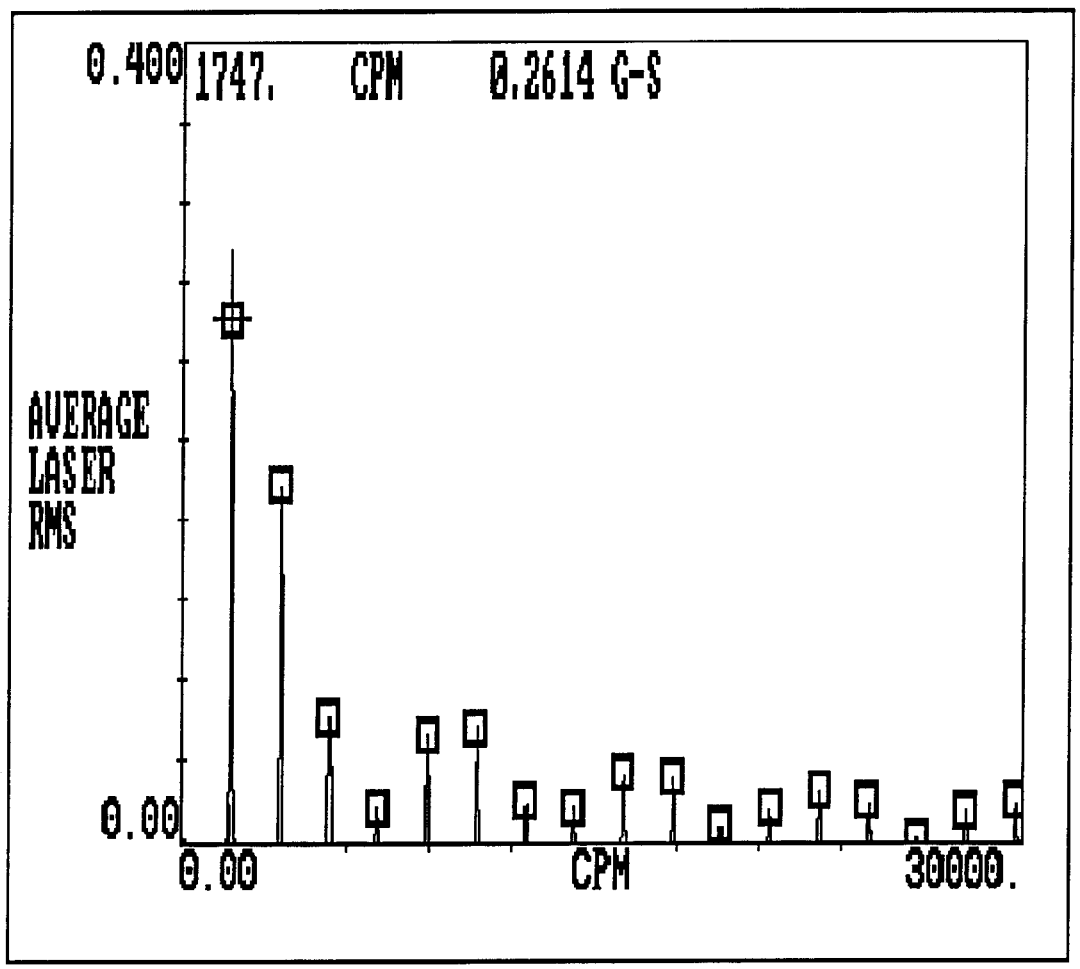
FIG. 9 is a spectral plot output from the system depicting the turning speed produced from a simulated input signal.

The analyzer 28 then preferably uses the peak fit algorithm 54 to mark the peak, enhancing the accuracy of the "best approximation", while also enabling moving harmonic cursors (FIG. 9). The user is now able to verify the rotational speed of the object 12 by pressing 'Set RPM' on the analyzer 28, or the cursor can be manually moved to mark another peak. The cursor can also be moved by pressing the 'F4'or 'DVIDE PEAK' keys, bringing up a menu that asks the user to enter an integer. The "best approximation" frequency is divided by the integer and the new peak marked. This option is useful in cases where multiple gear teeth or fan blades are present. If no peaks are found or if no peaks match the criteria, then the original spectrum will be displayed to the user with the cursors turned off.

Figure 10:
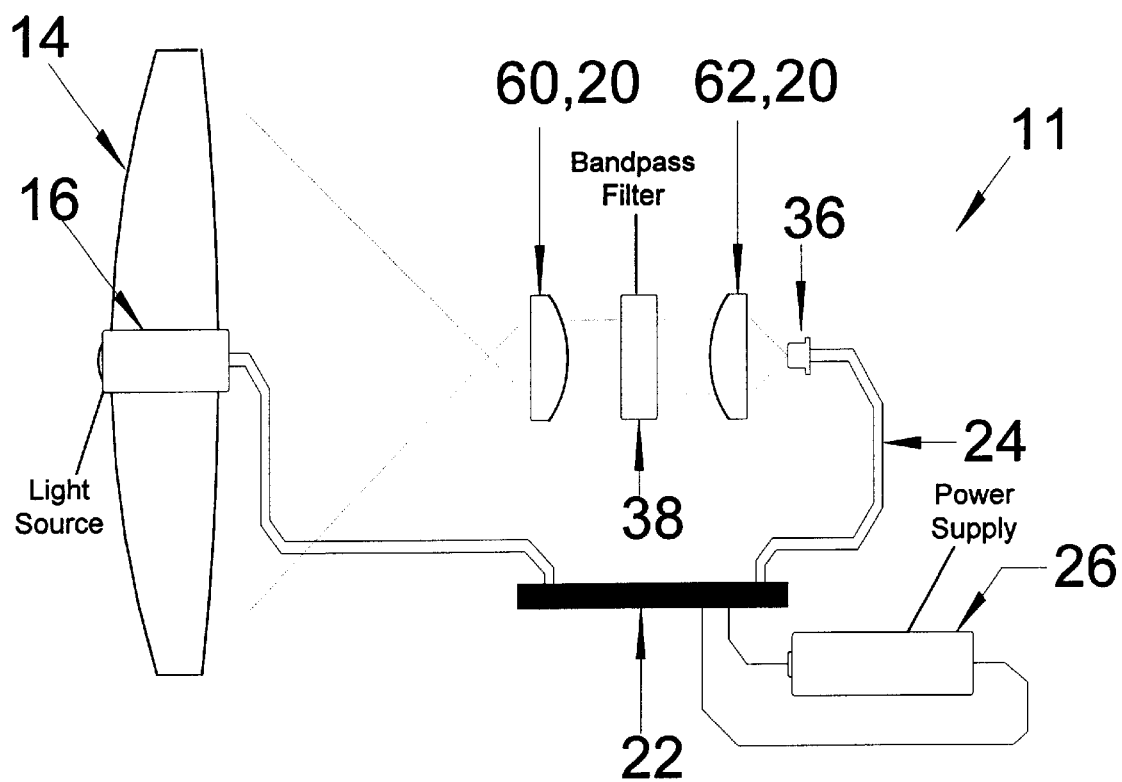
FIG. 10 is a side-view of another embodiment of an optical speed sensor.

Having described the determination of the speed of a rotating object 12 using the system 10, referring now to FIG. 10, a depiction of an alternative implementation of the focusing member 20 is shown. A second plastic lens 60 of approximately 12 millimeters in diameter, and being of plano-convex design, is located a distance behind the collecting lens 14. The second lens 60 has a focal length of about ¼ of the focal length of the collecting lens 14. The distance between the collecting lens 14 and second lens 60 is adjusted to form a collimated output beam from the second lens 60.

The collimated beam is necessary to produce nearly parallel rays for most efficient operation of the optical filter 38, which is preferably located a short distance behind the second lens 60. Only the portion of the collimated light which is in a narrow spectral range centered at a wavelength of about 650 nanometers, passes through the filter 38. A third lens 62, being identical in parameters to the second lens 60, is preferably located a short distance behind the optical filter 38. The third lens 62 focuses the collimated beam exiting the optical filter 38 onto the active area of a photodiode 36. The photodiode 36 is responsive to the laser light at about 650 nanometers. As described above, the photodiode 36 converts the light intensity patterns to electrical time domain signals, which are made available for signal processing.

Figure 11:
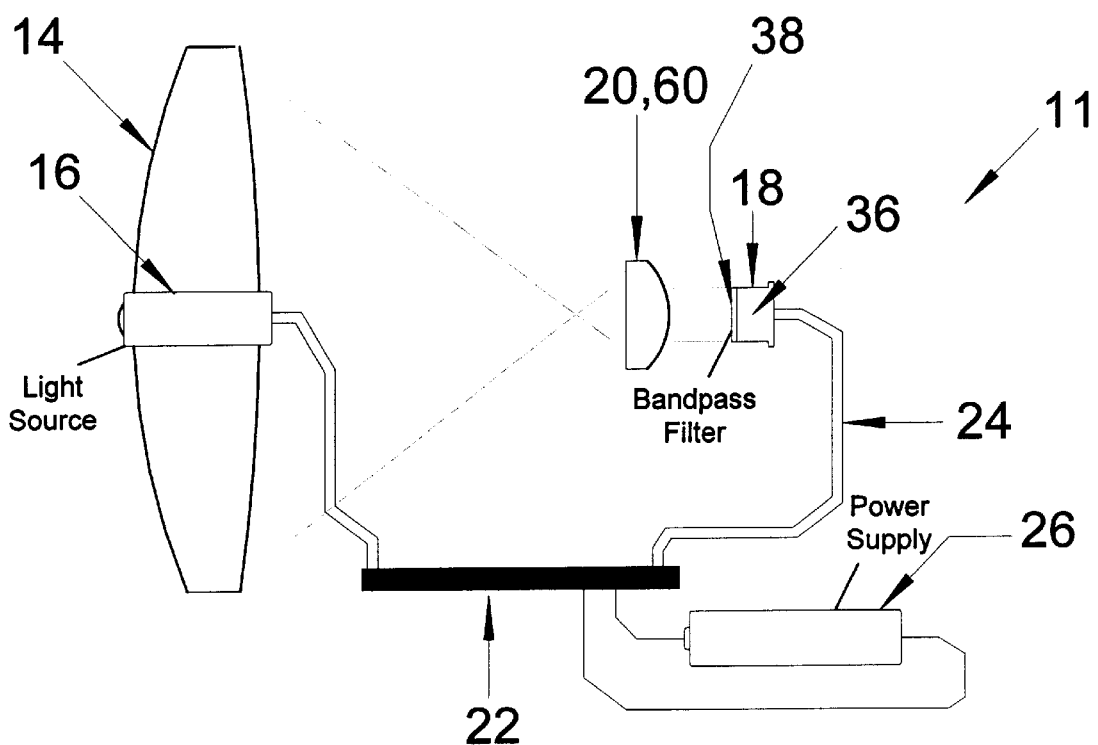
FIG. 11 is a side-view of yet another embodiment of an optical speed sensor.

As shown in FIG. 11, yet another embodiment of the focusing member 20 is shown. The third lens and the separate optical bandpass filter are eliminated by using a photodiode 36 with an integral optical bandpass filter 38, i.e. the detector 18 as described above. Preferably, the photodiode 36 has an active area of approximately four millimeters$^2$. The distance between the collecting lens 14 and the second convex lens 60 is adjusted so that the exiting light beam is collimated or slightly converging, so that substantially all of the received radiant flux is incident upon the active area of the photodiode 36. It is preferred that the converging beam does not exceed a half angle of greater than ten degrees with respect to the coaxial center of the optical system.

Figure 12:
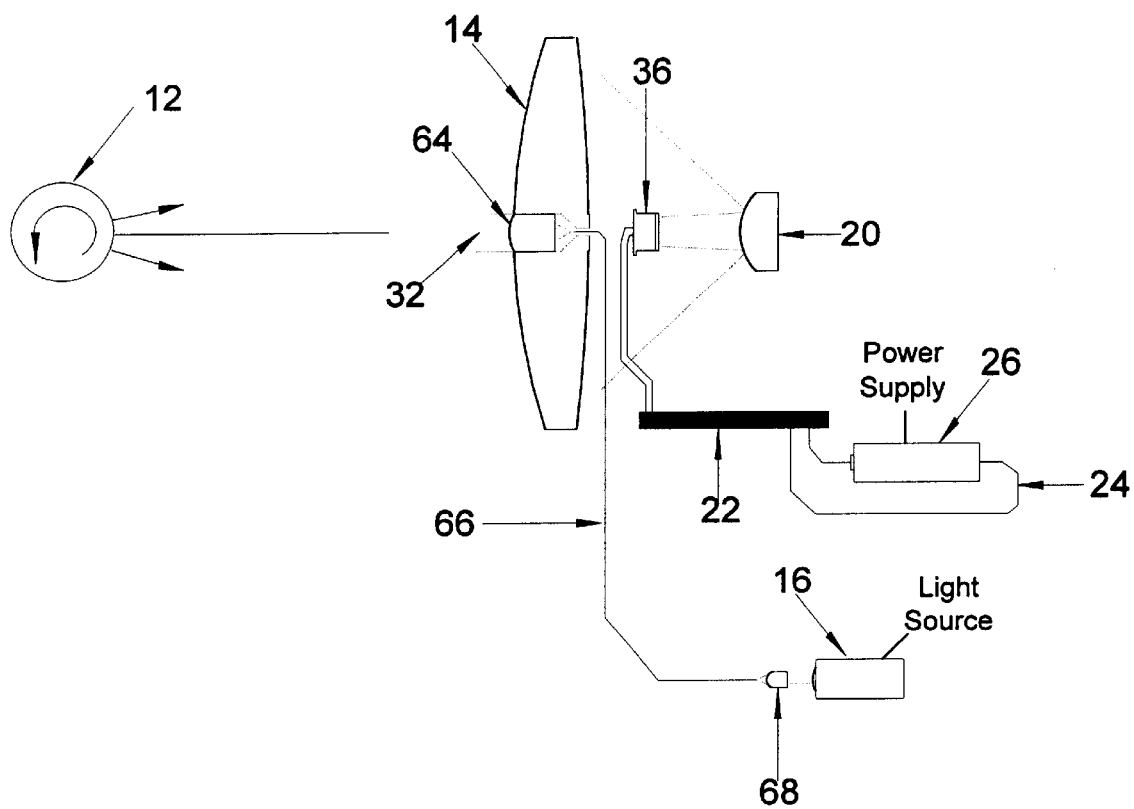
FIG. 12 is a side-view of another embodiment of an optical speed sensor.

As shown in FIG. 12, a variation applicable to the embodiments described above is described. The light source 16 is preferably relocated. For example, a laser module, such as the module described above, may be housed anywhere within an enclosure proximate the optical system or circuitry. Alternatively, the laser module may be housed in a location remote from the instrument. In both instances, a small collimating lens 64 is installed in the center bore 32 of the collecting lens 14 proximate the location previously occupied by the light source 16. A fiber optic member 66 conveys the radiant flux from the light source 16 to the small collimating lens 64, wherein the collimating lens 64 directs the light beam to the target area of the rotating object 12. A small coupling lens 68 is used to properly focus the light source 16 into the input end of fiber optic member 66.

This construction lends at least two advantages. First, locating the light source 16 offsite allows greater flexibility in the mechanical construction of the optical speed sensing system 10. Second, since visible semiconductor lasers are limited as to maximum operating temperatures compared to most general semiconductor devices, the light source 16 can be located in a cooler environment, being coupled by the fiber optic member 66 to the collecting lens 14.

Figure 13:
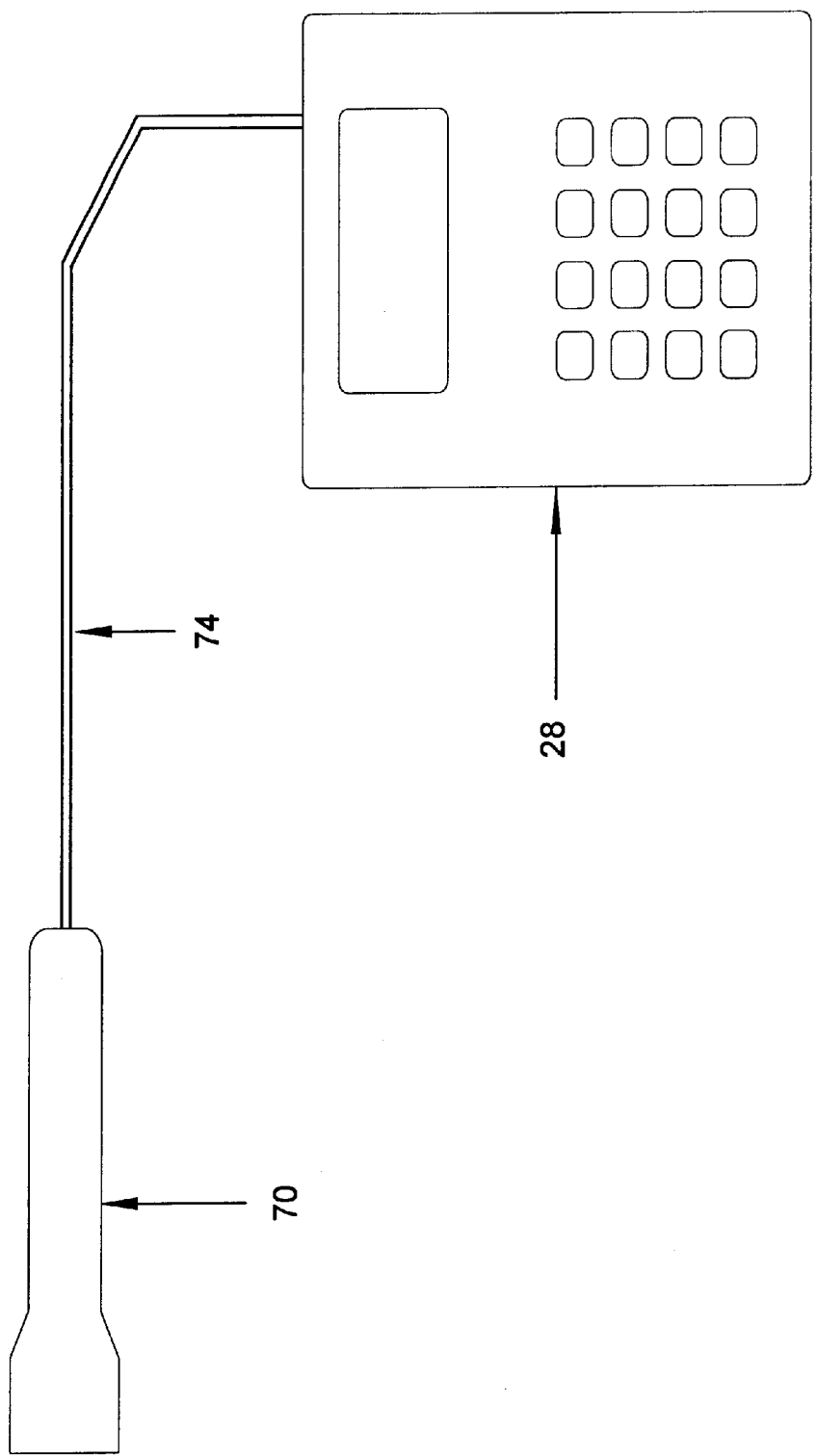
FIG. 13 depicts a preferred embodiment of an optical speed sensing system.

Most preferably, as shown in FIG. 13 the optical speed sensing system 10 includes a sensor housing 70 containing the optical processing and analog signal conditioning components, and a portable analyzer 28 for digitally processing the analog signals to provide a speed indication to a user of the optical speed sensing system 10. A cable 74 provides the electrical path for the provision of power from the analyzer 28 to the components contained within the sensor housing 70. The cable 74 also operates to carry the analog signals to the analyzer 28. It will be appreciated that a battery can be provided internally within the sensor housing 70 and a suitable wireless communication system provided for transferring data to the analyzer 28.

Figure 14:
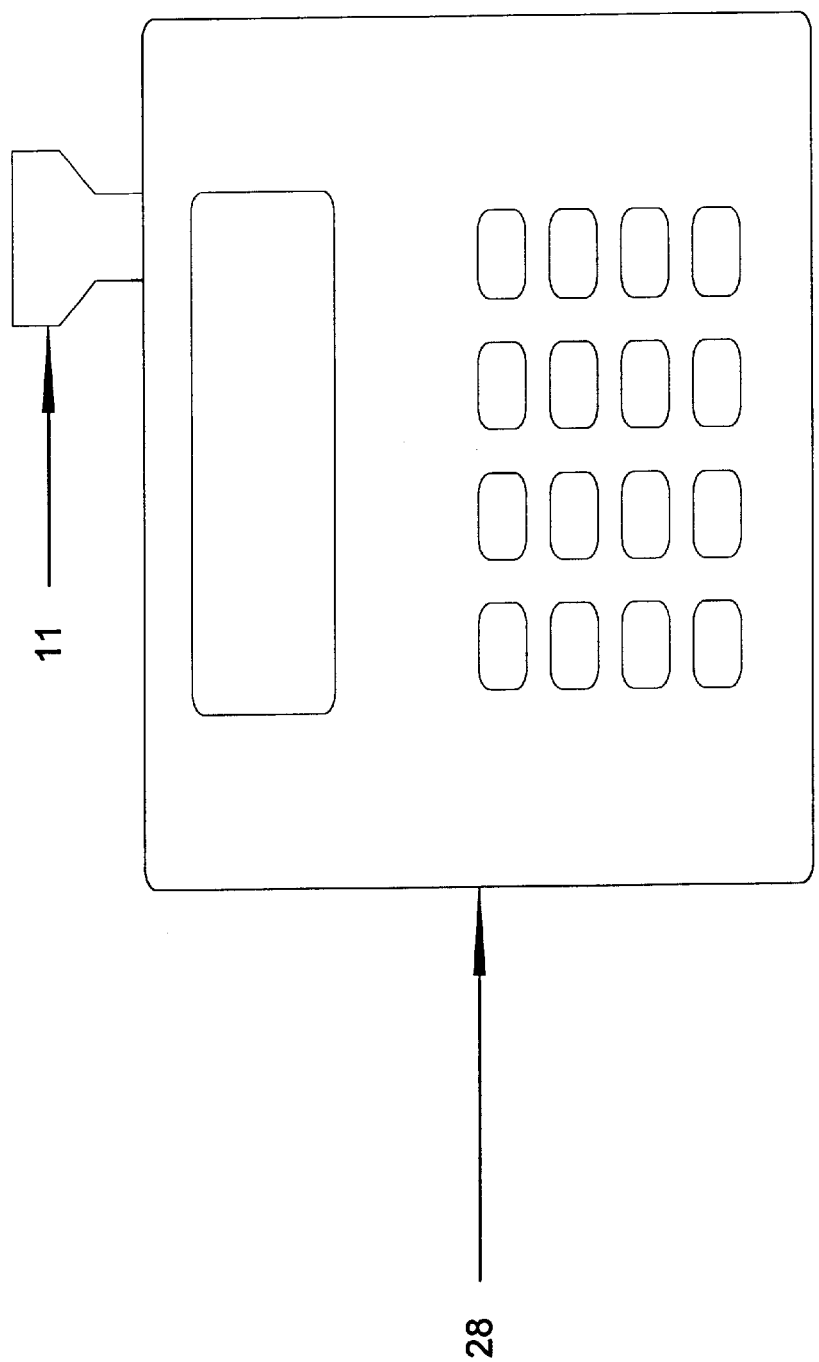
FIG. 14 depicts another aspect of an optical speed sensing system.
Figure 15:
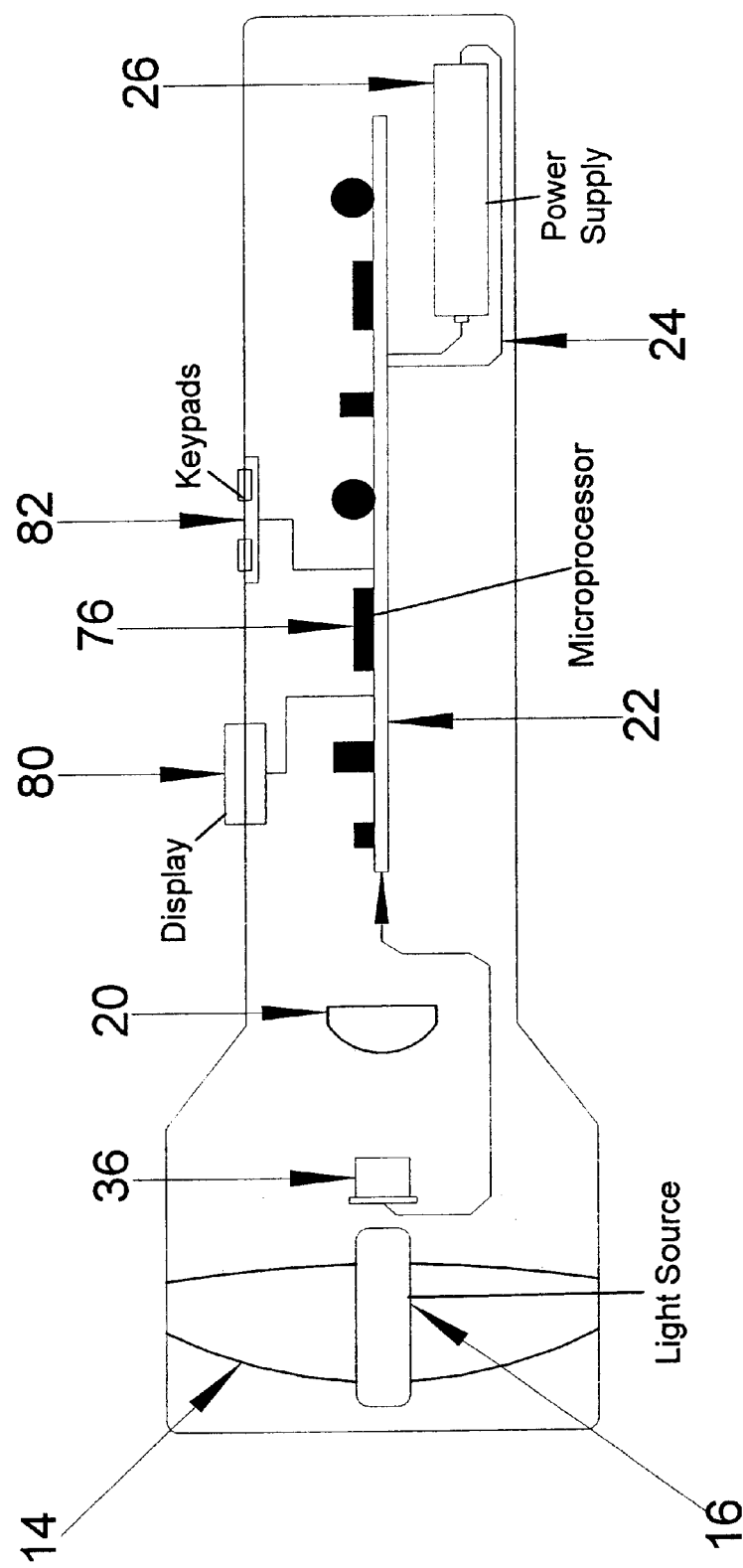
FIG. 15 depicts yet another aspect of an optical speed sensing system.

As shown in FIG. 14, in accordance with another aspect of the system 10, the optical speed sensor 11 and electronics are included in the analyzer housing to form a single handheld unit. Also, with reference to FIG. 15, a microprocessor 76 can be included on the circuit board 22, wherein the microprocessor 76 performs the finction of the analyzer 28. Additionally, display 80 and keypad 82, may be included for the user interface. Thus, a speed indication can be provided in one compact unit without requiring an external analyzer.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally, and equitably entitled.

What is claimed is:

1. An apparatus for determining a rotational speed of a rotating object without requiring a reflective target on the object, the apparatus comprising:

a light source for transmitting a collimated light beam having a selected wavelength directly at the rotating object, wherein light signals are reflected from the rotating object, an optical system for focusing the reflected light signals onto a detector having a single detection region, wherein the detector detects the focused light signals and generates electrical signals based thereon, a power source for providing power to the apparatus, and an analyzer including at least one Fourier Transform function for transforming the electrical signals, the analyzer for processing the electrical signals representative of the reflected light signals, determining, and outputting the rotational speed of the object from the transformed signals.

2. The apparatus of claim 1 wherein the analyzer further comprises a first Fourier Transform means operable to produce a power spectral density (frequency) spectrum.

3. The apparatus of claim 2 further comprising display means for displaying the power spectral density spectrum as a speed spectrum.

4. The apparatus of claim 2 wherein the analyzer further comprises a second Fourier Transform means operable to convert power spectral density data to autocorrelation data.

5. The apparatus of claim 2 wherein the analyzer further includes a peak fit algorithm for fitting a curve to the spectrum including higher order peaks in a harmonic family generated by the Fourier Transform function, further enhancing the speed determination.

6. The apparatus of claim 1, wherein the optical system further comprises:

a collecting lens for collecting reflected light signals from the rotating object, and a focusing member for focusing the collected light signals onto the single detection region of the detector.

7. The apparatus of claim 6 wherein the focusing member is a convex spherical or hyperbolic mirror.

8. The apparatus of claim 6 wherein the collecting lens is a substantially aspheric lens having a diameter of between about 30 millimeters to about 50 millimeters and including a central bore for mounting the light source therein.

9. The apparatus of claim 6 wherein the focusing member includes:

a second lens having a smaller diameter and focal length relative to the collecting lens, for collimating the light collected by the collecting lens, an optical filter located relative to the second lens for filtering the light collimated by the second lens, and a third lens for focusing the filtered light onto an active area of the detector.

10. The apparatus of claim 1 wherein the detector comprises a photodiode having an active area of about 4 millimeters$^2$ including an integral optical bandpass filter having a passband centered at about 650 nanometers and having a bandwidth of about 20 nanometers and the light source is a visible light laser diode micro module operating at a wavelength of about 650 nanometers.

11. The apparatus of claim 1 wherein the analyzer further comprises a microprocessor including digital processing components for digitizing the electrical signals generated by the detector and firmware algorithms for processing the digitized signals, the microprocessor automatically determining and outputting the rotational speed of the rotating object based on the processed digitized signals.

12. A method for determining a rotational speed of a rotating object comprising the steps of:

(a) providing an apparatus including a light source, an optical system, a detector having a single detection region, a power source for providing power to the apparatus, and an analyzer including a Fourier Transform function operable to perform at least one Fourier Transform, (b) transmitting a collimated light beam having a selected wavelength with the light source directly at the rotating object, wherein light signals are reflected from the rotating object, (c) focusing the reflected light signals onto the single detection region of the detector, (d) detecting the focused light signals with the detector, (e) generating electrical signals based on the light signals detected with the single detection region of the detector, (f) processing the electrical signals with the analyzer including at least one operation with the Fourier Transform finction, (g) determining the rotational speed of the rotating object with the analyzer from the processed electrical signals, and (h) outputting the rotational speed of the object to a user with the apparatus.

13. The method of claim 12 wherein the step of processing the electrical signals further comprises the steps of:

(f1) digitizing the electrical signals with digital processing components included in the analyzer, (f2) applying the Fourier Transform function to the digitized signals producing a spectrum, and (f3) generating autocorrelation data from a second application of the Fourier Transform function.

14. The method of claim 12 wherein the step of determining the rotational speed of the object further comprises the steps of:

(g1) storing peak magnitude data determined from data generated from a last application of the Fourier Transform finction in a number of frequency bins included in the analyzer, (g2) determining a number of largest magnitude peaks with a peak location algorithm included in the analyzer from the stored peak magnitude data, (g3) locating a first peak within the number of largest magnitude peaks determinative of the rotational speed of the object, and (g4) determining whether the first peak satisfies selected criteria.

15. The method of claim 14 further comprising the steps of:

(g5) determining whether the first peak is not located in one of a first set of frequency bins, (g6) determining whether an amplitude of the first peak is greater than about 0.30 multiplied by a largest amplitude peak located in any other frequency bin, (g7) determining whether a second peak is located at about two times a frequency of the first peak which is not located in one of the first set of frequency bins and an amplitude of the second peak is greater than about 0.30 multiplied by the largest amplitude peak located in any other frequency bin, and (g8) using the first peak to determine the rotational speed of the object when steps (g5)–(g7) are satisfied.

16. The method of claim 15 further comprising the steps of:

(g9) determining from the stored peak magnitude data whether an amplitude of a third peak having a frequency is greater than about 0.90 multiplied by the amplitude of the first peak, (g10) determining if a fourth peak located at about two times the third peak frequency also satisfies step (g9), (g11) using the third peak to determine the rotational speed of the object when steps (g9)–(g10) are satisfied.

17. The method of claim 12 further comprising the steps of:

(i) digitizing the electrical signals with digital processing components included in the analyzer, and (j) applying a Fourier Transform function included in the analyzer to the digitized signals, (k) creating a spectrum with the Fourier Transform function, the spectrum including data representative of the rotational speed of the object, and (l) determining the rotational speed of the object from a user selected peak.

18. An apparatus for determining a rotational speed of a rotating object comprising:

optical processing components, including:
  a light source for transmitting a collimated light beam having a selected wavelength at the rotating object, wherein light signals are reflected from the rotating object, and
  an optical system for focusing the reflected light signals onto a detecting means having a single detection region, wherein the detecting means is operable to detect the focused light signals and generate a detected light signal based on light detections with the single detection region of the detector, an analyzer for digitizing the detected light signal to produce a digitized detected light signal, including a Fourier Transform function for converting the digitized detected light signal from a first domain to a second domain providing a spectrum including data representative of the rotational speed of the object, the analyzer for analyzing the spectrum to determine the rotational speed of the object and producing an output indicating the rotational speed of the rotating object, and a power source for providing power to the apparatus.

19. The apparatus of claim 18, wherein the analyzer further comprises a peak location algorithm for locating a fundamental frequency peak of the data generated by the Fourier Transform function, wherein the analyzer determines the rotational speed of the object from the fundamental frequency peak of the spectrum.

20. The apparatus of claim 18, wherein the analyzer further comprises firmware for applying the Fourier Transform function successively to generate data representative of the rotational speed of the object, the analyzer determining the rotational speed of the object from data generated from a last application of the Fourier Transform function.

21. The apparatus of claim 19 wherein the analyzer determines the rotational speed of the object based in part on a user selected peak.

22. An optical speed sensing system for manually determining the speed of a rotating object without requiring a reflective element on the object, the system comprising:

a collimated light source of a selected wavelength for illuminating an area of the rotating object, wherein light signals are reflected from the rotating object, an optical system for collecting the reflected light signals of the selected wavelength and rejecting light signals other than the selected wavelength, wherein the collected light signals are converted to electrical signals, a conversion means for digitizing the electrical signals, an analysis means including a Fourier Transform function for generating power spectral density data from the digitized electrical signals, the power spectral density data being stored in a first memory, a means for displaying a speed spectrum to a user of the system, wherein the speed spectrum is generated from the power spectral density data stored in the first memory and, a calculation means for calculating the rotational speed of the rotating object according to a frequency peak in the displayed speed spectrum, the frequency peak being selected by a user of the system.

23. An optical speed sensing system for automatically determining the speed of a rotating object without requiring a reflective element on the object, the system comprising:

a collimated light source of a selected wavelength for illuminating an area on the rotating object, wherein light signals are reflected from the rotating object, an optical system for collecting the reflected light signals of the selected wavelength and rejecting light signals other than the selected wavelength, wherein the collected light signals are converted to electrical signals, a conversion means for digitizing the electrical signals, an analysis means including:

a Fourier Transform means for applying a first Fourier Transform function to generate power spectral density data from the digitized electrical signals, the power spectral density data being stored in a first memory, and for applying a second Fourier Transform function converting the power spectral density data to autocorrelation data, the autocorrelation data being stored in a second memory, and an algorithm means operable upon the stored autocorrelation data, wherein the algorithm means includes criteria for automatic determination of the rotational speed of the rotating object from the autocorrelation data, and means for displaying a speed spectrum to a user of the system, wherein the speed spectrum is generated from the power spectral density data stored in the first memory, the display of the speed spectrum indicating the rotational speed of the rotating object.

24. The system of claim 23 wherein the algorithm means includes first criteria for locating a first peak having a first frequency and amplitude, the first peak indicating the rotational speed of the rotating object, the first criteria requiring:

a. that the first peak is not located in one of a first set of frequency bins, b. that the first peak amplitude is greater than about 0.30 multiplied by a largest amplitude of a selected bin, and c. that there is a second peak located at about two times the first peak frequency (+or−Delta-F) also satisfying A and B.

25. The system of claim 24 wherein the algorithm means includes second criteria requiring:

d. that a third peak having a frequency has an amplitude greater than about 0.90 multiplied by the amplitude of the first peak, and e. that there is a fourth peak located at about two times the third peak frequency (+or−Delta-F) also satisfying D.

* * * * *